United States Patent [19]

Desy et al.

[11] Patent Number: 4,856,109
[45] Date of Patent: Aug. 15, 1989

[54] FACE PROTECTIVE DEVICE

[75] Inventors: Raoul O. Desy, Fiskdale; James J. Krusas, Sturbridge, both of Mass.

[73] Assignee: American Optical Corporation, Southbridge, Mass.

[21] Appl. No.: 187,055

[22] Filed: Apr. 27, 1988

[51] Int. Cl.$^4$ .............................................. A61F 9/06
[52] U.S. Cl. .............................................. 2/9; 2/424
[58] Field of Search ............................ 2/8, 9, 206, 424; 403/107, 108, 329, 330

[56] References Cited

U.S. PATENT DOCUMENTS

| | | | |
|---|---|---|---|
| 2,706,815 | 4/1955 | Parmelee | 2/441 |
| 2,729,820 | 1/1956 | Anderson | 2/9 X |
| 2,758,307 | 8/1956 | Treiber | 2/9 |
| 2,829,374 | 4/1958 | Malcom, Jr. | 2/9 |
| 3,214,767 | 11/1965 | Weber | 2/9 |
| 3,475,766 | 11/1969 | Raschke | 2/9 |
| 3,649,107 | 3/1972 | Hoffmaster et al. | 403/107 X |
| 3,686,690 | 8/1972 | Webb | 2/9 |
| 3,696,442 | 10/1972 | Amundsen et al. | 2/8 |
| 3,866,244 | 2/1975 | Ruck | 2/8 |
| 3,868,727 | 3/1975 | Pascall | 2/8 |
| 4,047,353 | 9/1977 | Aarons | 403/107 X |
| 4,199,823 | 4/1980 | Jenkins et al. | 2/424 |
| 4,625,341 | 12/1986 | Broersma | 2/9 X |

FOREIGN PATENT DOCUMENTS 233429  5/1925  United Kingdom ............... 403/108

*Primary Examiner*—Werner H. Schroeder
*Assistant Examiner*—Jeanette E. Chapman
*Attorney, Agent, or Firm*—Fishman, Dionne & Cantor

[57] ABSTRACT

A transparent faceshield for protecting the face and eyes from impact and the like is detachably connected to an arcuate visor or crown using detents integrally molded to the crown and corresponding through-holes in the faceshield which receive and engage the detents. The use of integrally molded detents permits removable attachment of the faceshield to the crown without the necessity for secondary operations or discrete assembly hardware thus providing a system which is easily assembled and disassembled by the end user.

14 Claims, 2 Drawing Sheets

FACE PROTECTIVE DEVICE

BACKGROUND OF THE INVENTION

This invention relates generally to face protective devices of the type employing a visor or crown and a faceshield carried by the crown. More particularly, this invention relates to a crown/faceshield combination wherein the faceshield is removably attachable to the crown without the necessity for secondary operations or discrete assembly hardware thus providing a system which is easily assembled and disassembled by the end user.

Face protective devices of the type hereinabove discussed are well-known and utilize known headgear comprised of a resilient adjustment head band which is articulated to a visor or crown. Attached to the crown is a light weight, transparent plastic shield which is adapted to be supported in front of the face. Such devices are for general utility as protective means for both the face and the eyes of the wearer when the wearer is subjected to the hazards of flying particles such as in lath or grinding operations, to heat in connection with general work around furnaces, or when subjected to the hazards of splashing chemicals or the like. It will be appreciated that such face protective devices must not only be extremely light in weight and comfortable to wear, but also must enable the interchanging of face shields when they become pitted or otherwise rendered impractical for use.

Typically, the visor or crown is made of a molded plastic material and the faceshield is either molded or made from sheet stock in a known manner. In either case, secondary manufacturing processes must be utilized to attach discrete fastening hardware to either one or both of the crown and faceshield. For example, in U.S. Pat. No. 3,763,495 to De Angelis, a secondary manufacturing process consisting of a riveting step is carried out to rivet a transparent faceshield to a crown. Similarly, in U.S. Pat. No. 2,610,323 to Johnson, discrete snap-action means have to be provided to a crown and faceshield to permit attachment therebetween.

It will be appreciated that the assembly required in secondary manufacturing processes leads to high manufacturing costs both for the additional labor time in completing the secondary manufacturing process as well as for the necessity of Purchasing discrete attachment hardware.

While prior art face protective devices are known wherein the crown and faceshield are unitary and therefore require no separate secondary hardware, such Prior art face protective devices are not particularly desirable since such designs do not allow for faceshield replacement.

SUMMARY OF THE INVENTION

The above-described deficiencies and drawbacks of the prior art are overcome or alleviated by the crown/faceshield assembly of the present invention. In accordance with the present invention, known resilient headgear is pivotably attached in a known manner to a curved visor like portion or crown. A transparent faceshield is then detachably attached to the crown. An important feature of the present invention is that no secondary manufacturing processes are necessary to attach the faceshield to the crown. Instead, integrally molded detents are provided to the crown. In turn, openings are provided at appropriate locations in the faceshield which will mate to each of the detents in the crown. Thus, the crown/faceshield combination of the present invention can each be molded complete in one molding operation without the need for assembly hardware or secondary operations. By means of the integrally molded detents, no hardware is needed to attach the faceshield to the crown. It will be appreciated that the detents can be either integrally molded into the crown or the faceshield or both.

The present invention includes several advantages over prior art methods of attaching headgear and faceshields. For example, by obviating hardware, such as rivets, snaps, mounting posts, etc., the present invention utilizes fewer pieces and therefore has lower materials cost. In addition, preclusion of the secondary operations lead to less manufacturing and labor operations needed to attach the hardware.

The above-discussed and other features and advantages of the present invention will be appreciated and understood by a person of ordinary skill in the art from the following detailed description and drawings.

BRIEF DESCRIPTION OF THE DRAWINGS

Referring now to the drawings, wherein like elements are numbered alike in the several FIGURES.

DESCRIPTION OF THE PREFERRED EMBODIMENT

Figure 1:
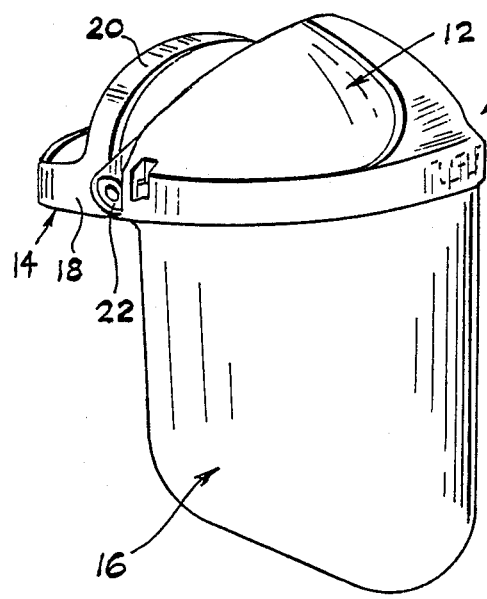
FIG. 1 is a perspective view of the face protective device of the present invention.
Figure 2:
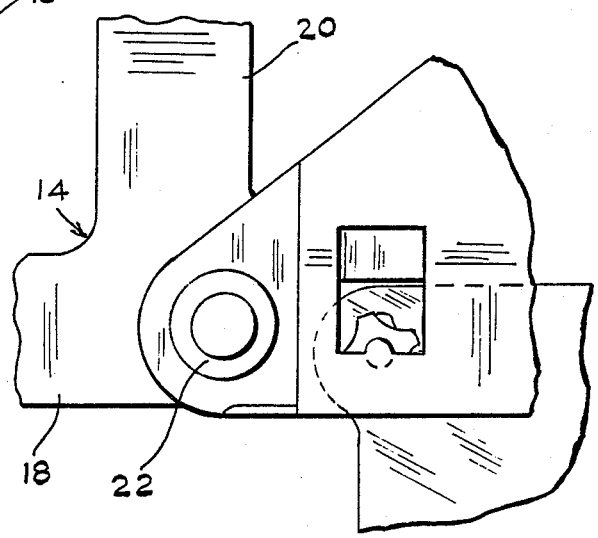
FIG. 2 is an enlarged side elevation view of a portion of the faceshield of FIG. 1 depicting a detachable connection between the crown and faceshield.

Referring first to FIG. 1, a face protective device in accordance with the present invention is shown generally at 10. Face protective device 10 is comprised of three primary parts including a visor-like portion or crown 12, a headband 14 pivotably attached to crown 12 and a curved transparent faceshield 16 detachably connected to crown 12. Headband 14 has a well known construction and is comprised of a one-piece member molded from a resilient plastic material. Headband 14 includes a circular band 18 having well known means for adjustment of the circumference (not shown) as well as a cross-member 20 which also includes a well-known adjusting means for sizing headband 14 to a preselected circumference and depth to thus achieve a snug and comfortable fit on a person's head. Headgear 14 is pivotably mounted to crown 12 by use of a pair of rivets 22 in a well known mounting procedure. Referring jointly now to FIGS. 1-6, visor-like portion or crown 12 has an arcuate main surface which should substantially conform to the upper forehead. At the edge corresponding to the lower forehead area, crown 12 includes an inner edge 24 and an outer edge 26 which is similarly shaped substantially to conform to the curvature of the lower forehead. Inner and outer edges 24 and 26 are spaced apart to define a recess 28. It will be appreciated that inner edge 24 terminates slightly prior to outer edge 26 to define a lead-in portion for receiving faceshield 16.

An important feature of the present invention is the provision of integrally molded detent structures on crown 12 which receive and lock to appropriate through-holes or openings in faceshield 16. In a preferred embodiment, three detents are utilized including a pair of opposed star shaped detents 30 integrally molded in outer edge 26 and a single wedge shaped detent 32 extending from inner edge 24. Detents 30 are each located on opposed sides of crown 12 and extend inwardly towards the interior of crown 12 from outer edges 26., Preferably, detents 30 comprise a shaft or cylindrical base 33 having a star shaped or multi-cornered head 34. While the drawings show use of a four pointed star head 34, it will be appreciated that any number of star points may be utilized. Above each star shaped detent 30 is a window 36 molded through crown 12. As will be discussed below, window 36 is important for Providing visibility during the assembly of the crown and the faceshield. Window 36 is preferably rectangular and is positioned such that the upper portion of detent 30 will be exposed through window 36 from the exterior of the crown.

Figure 7:
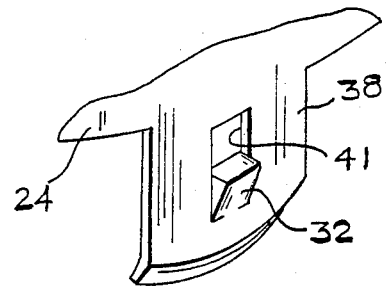
FIG. 7 is an enlarged prospective view of a snap action detent integrally molded into the crown.
Figure 7A:
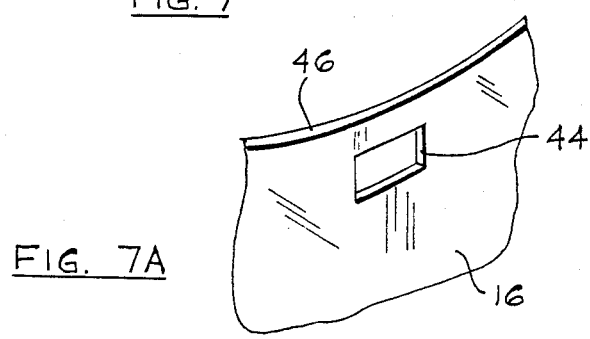
FIG. 7A is an enlarged prospective view of a rectangular through hole in the faceshield which receives the detent of FIG. 7.

As mentioned, crown 12 also includes wedge shaped detent structure 32 which is more clearly shown in FIG. 7. Unlike the star detent 30 on opposed sides of crown 12, detent 32 comprises a wedge or ramp extending outwardly from a lip 38 which depends downwardly from inner edge 24. Lip 38 is substantially coterminous with outer edge 26 and includes a diverging end portion 40 which acts as a lead-in portion for faceshield 16. As in detents 30, detent 32 includes an opening or window 41 lip 38 which provides ease of installation when locking detent 32 to a corresponding opening in the faceshield.

Faceshield 16 has a well known arcuate or curved shape for protecting the face of the wearer from sparks and other flying debris. Faceshield 16 may be either molded or made from sheet stock. In any event, faceshield 16 is provided with a plurality of openings which are adapted for inter locking engagement to matching detents in crown 12. The opposed sides of faceshield 16 include facing openings or through-holes 40 which have a shape which is complimentary to the shape of detent 30 in crown 12. Thus, for example, as clearly shown in FIGS. 3, 4 and 6, openings 40 have a four cornered star shape. It will be appreciated that each opening 40 is slightly larger than each star shaped head 34 of detent 30 to permit detent 30 to pass through opening 40. Faceshield 16 also includes a wing portion 42 which extends outwardly from the remaining side edge of faceshield 16. It will be appreciated that opening 40 is located in wing portion 42 for ease of assembly as will be discussed below. At the front of faceshield 16 along the upper edge 46 thereof, a rectangular opening or through-hole 44 is provided. Rectangular opening 44 is sized to permit locking engagement with the wedge shaped detent structure 32 in crown 12.

Figure 3:
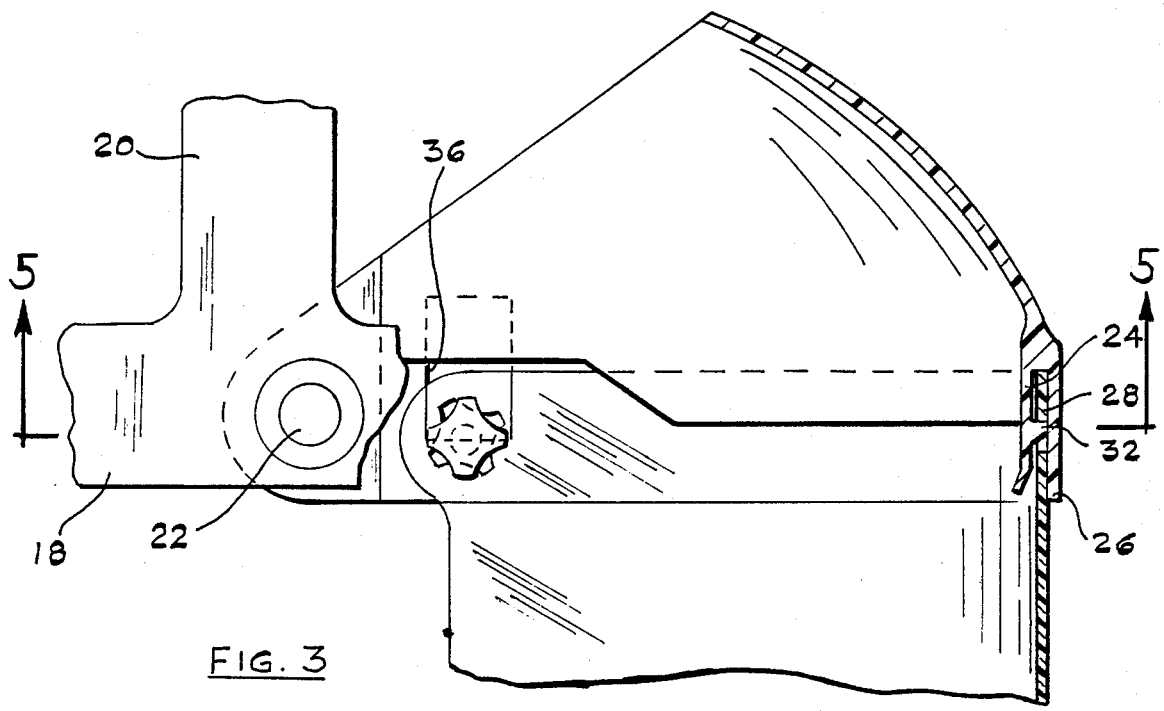
FIG. 3 is a cross-sectional elevation view along the line 3—3 of FIG. 1.
Figure 4:
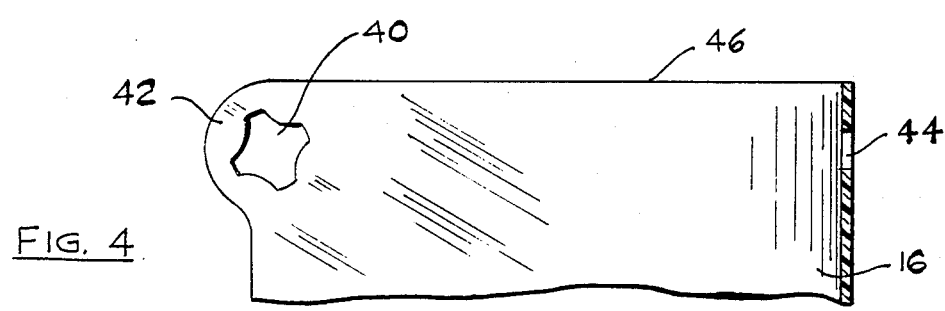
FIG. 4 is a cross-sectional elevation view of a portion of a faceshield shown at FIG. 1.
Figure 5:
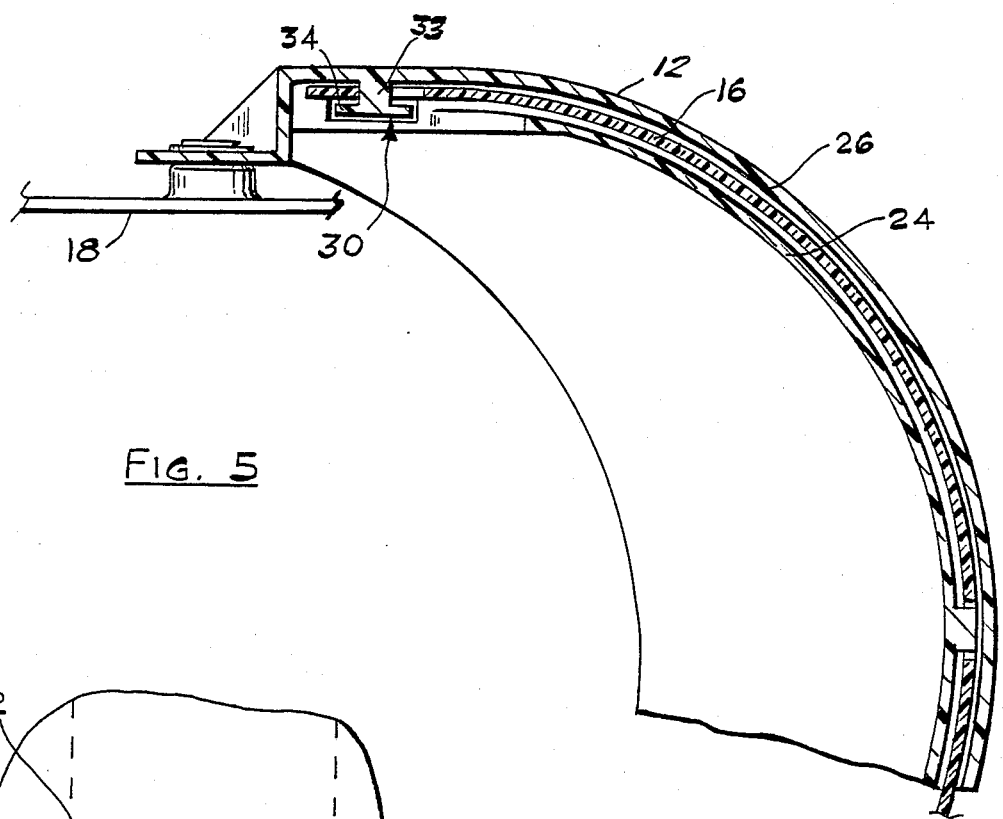
FIG. 5 is a cross-sectional elevation view along the line 5—5 of FIG. 3.
Figure 6:
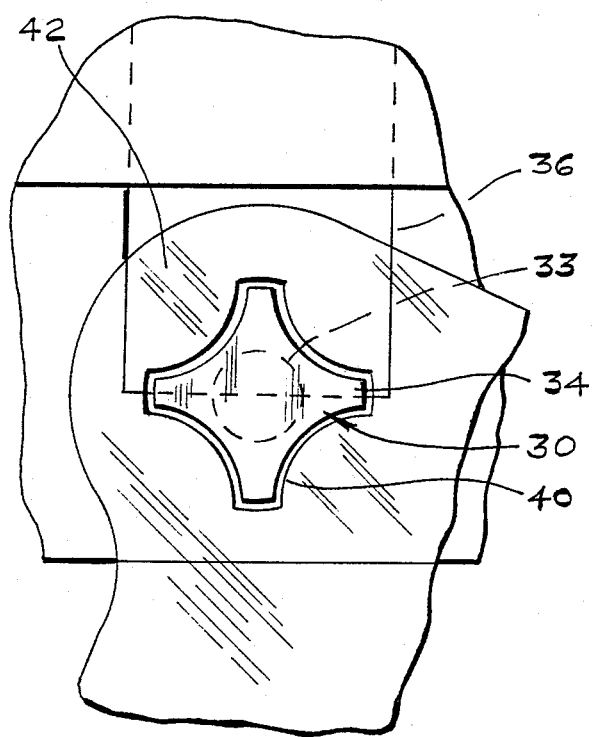
FIG. 6 is an enlarged view of the detent structure during the initial assembly step between the faceshield and crown.

The assembly between the crown 12 and faceshield 16 will now be described. Turning first to FIG. 6, faceshield 16 is initially aligned with crown 12 such that the pointed corners 34 of star 30 are in mutual alignment with the pointed corners of opening 40. At this point, faceshield 16 will be at an angle with respect to crown 12. It will be appreciated that wings 42 help permit this initial angular alignment between opening 40 and detent 30 as shown in FIG. 6. Next, the sides of resilient faceshield 16 are urged outwardly so that detents 30 pass through openings 40. As a result, openings 40 will rest on shafts 33 of detents 30. At this point, faceshield 16 is pivoted upwardly along shaft 33 of detent 30 so that the pointed corners of opening 40 will be out of alignment with the pointed corners 34 of detent 30. Simultaneously, the upper edge 46 of faceshield 16 is received within the recess 28 between depending edges 24 and 26. As faceshield 16 is received within recess 28, wedge shaped detent 32 and depending member 38 will slightly deflect outwardly and then snap back intthrough-hole 44 of faceshield 16 as shown in FIG. 3. At this point, faceshield 6 will be firmly engaged to crown 12 and will be held tightly therein by the peripheral recess 28, detent 32, and the pair of opposed detents 30. Note that in this final assembly, the pointed star shaped corners 34 of detent 30 will be out of sync with the star shaped corners of opening 40 so that detent 30 will bear against faceshield 16 and preclude disengagement. It will be appreciated that a star shaped side detent (as opposed to the wedged shape front detent 30) may be preferable because of the large bearing area provided for retaining the shield against side impacts.

The face Protective device of the present invention includes several significant features and advantages relative to prior art face protective devices of this type. For example by means of the integrally molded detent structures in crown 12, no secondary hardware is needed to attach crown 12 to faceshield 16. Instead, the detents provide quick and easy assembly between the crown and faceshield. Also, the preclusion of additional hardware for attaching the faceshield to the crown obviates the additional manufacturing associated with assembly of hardware.

It will be appreciated that while the several detents have been shown as integrally molded to the crown, the detents could also be molded directly to the faceshield. In this latter case, the crown would include appropriate openings for receiving and locking to the detent structures on the faceshield. Similarly, detents could be provided on both the crown and faceshield. Thus, the present invention contemplates that either the crown or the faceshield or both would include the integrally molded detent features with the corresponding through-holes being located on the other corresponding pieces.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A face protective device comprising:
    a crown having an arcuate shape for covering the forehead, said crown having a lower peripheral edge;
    detent means integrally molded in said peripheral edge;
    a faceshield for covering the face, said faceshield having an upper edge;
    openings through said faceshield near said upper edge, the number of said openings corresponding to the number of said detent means, said openings being sized to receive said detent means and to effect detachable engagement to said detent means so as to detachably mate said faceshield to said crown.

2. The device of claim 1 wherein said lower peripheral edge of said crown includes:
an outer depending edge and an inner depending edge spaced from said outer edge to define a recess therebetween; and
said upper edge of said faceshield being received in said recess.

3. The device of claim 2 wherein:
said outer edge extends beyond said inner edge.

4. The device of claim 2 wherein said detent means includes:
a pair of opposed side detents extending toward each other from said outer edge.

5. The device of claim 4 wherein:
said side detents each comprise a shaft having a multi-cornered head thereon; and
said faceshield openings include a pair of opposed side openings corresponding to said side detents with said side openings having a multi-cornered configuration corresponding to said side detents.

6. The device of claim 5 including:
a pair of opposed side windows through said crown, said opposed side windows being adjacent said side detents.

7. The device of claim 5 wherein:
said faceshield has upper side corners and includes a pair of wings extending from said upper side corner; and
said side openings being positioned in said wings.

8. The device of claim 3 wherein said detent means includes:
a pair of opposed side detents extending toward each other from said outer edge.

9. The device of claim 8 wherein said detent means further includes:
a central detent extending towards said outer edge from a lip which depends downwardly from said inner edge.

10. The device of claim 9 wherein:
said lip is coterminous with said outer edge.

11. The device of claim 9 wherein:
said central detent has a wedge shape; and
said faceshield openings include a rectangular opening corresponding to said wedge shape central detent, said rectangular opening effecting a snap fit with said central detent.

12. The device of claim 9 including:
a central window through said crown, said central window being adjacent said central detent.

13. The device of claim 1 including:
headband means pivotably connected to said crown for attaching said crown to a head.

14. The device of claim 5 wherein:
said multi-cornered heads of said side detents are out of alignment with said multi-cornered openings when said faceshield is mated to said crown.

* * * * *